(12) United States Patent
Chokshi

(10) Patent No.: US 6,806,069 B2
(45) Date of Patent: Oct. 19, 2004

(54) UBIQUINONE COMPOSITION AND METHODS RELATED THERETO

(75) Inventor: Dilip Chokshi, Parsippany, NJ (US)

(73) Assignee: Pharmachem Laboratories, Inc., Kearney, NJ (US)

(*) Notice: Subject to any disclaimer, the term of this patent is extended or adjusted under 35 U.S.C. 154(b) by 0 days.

(21) Appl. No.: 09/757,222

(22) Filed: Jan. 9, 2001

(65) Prior Publication Data

US 2002/0128184 A1 Sep. 12, 2002

(51) Int. Cl.⁷ ............................. C12P 21/04; C12P 1/04; C12P 1/02; A61K 38/16
(52) U.S. Cl. ...................... 435/170; 435/171; 435/71.1; 514/8; 514/168; 424/234.1; 424/725
(58) Field of Search ................. 424/439, 400, 424/234.1, 246.1, 278.1, 94.1, 195.17, 195.16, 725, 780; 435/71.1, 170, 171; 514/8, 168

(56) References Cited

U.S. PATENT DOCUMENTS

| | | | |
|---|---|---|---|
| 3,196,018 A | | 7/1965 | Galler |
| 3,658,648 A | * | 4/1972 | Nakao et al. |
| 4,654,373 A | | 3/1987 | Bertelli |
| 5,008,118 A | | 4/1991 | Iwanami et al. |
| 5,298,246 A | * | 3/1994 | Yano et al. |
| 5,565,558 A | * | 10/1996 | McCully |
| 5,639,787 A | | 6/1997 | Riordan et al. |
| 5,747,071 A | | 5/1998 | Segall et al. |
| 5,804,555 A | * | 9/1998 | Tomita et al. |
| 5,891,469 A | | 4/1999 | Amselem |
| 5,895,652 A | * | 4/1999 | Giampapa |
| 5,912,272 A | | 6/1999 | Hoppe et al. |
| 5,950,634 A | | 9/1999 | Ochi et al. |
| 5,989,583 A | | 11/1999 | Amselem |
| 6,045,826 A | | 4/2000 | Borowy-Borowski et al. |
| 6,054,261 A | | 4/2000 | Masterson |
| 6,306,453 B1 | * | 10/2001 | Kurzinger |

FOREIGN PATENT DOCUMENTS

| | | | |
|---|---|---|---|
| GB | 2 178 662 A | * | 2/1987 |
| JP | 2000281586 A | * | 10/2000 |
| WO | WO 96/17626 | | 6/1996 |

OTHER PUBLICATIONS

Derwent 1991–295636 Sep. 1991 Derwent Kruzel.*
Derwent 1998–399777 Jul. 1998 Derwent Metz.*
Navarro, et al., "Protective Role in Ubiquinone in Vitamin E and Selenium–Deficient Plasma Membranes", *BioFactors 9*, pp. 163–170 (1999).
Hoppe, et al., "Coenzyme $Q_{10}$, a Cutaneous Antioxidant and Energizer", *BioFactors 9*, pp. 371–378 (1999).
Hodges, et al., "$CoQ_{10}$: Could It Have a Role in Cancer Management?", *BioFactors 9*, pp. 365–370 (1999).
Langsjoen, et al., "Overview of the Use of $CoQ_{10}$ in Cardiovascular Disease", *BioFactors 9*, pp. 273–284 (1999).
Baroni, et al., "Monounsaturated Diet Lowers LDL Oxidisability in Type Iib and Type IV Dyslipidemia Without Affecting Coenzymes $Q_{10}$ and Vitamin E Contents", *BioFactors 9*, pp. 325–330 (1999).
Pedersen, et al., "High Serum Coenzyme $Q_{10}$, Positively Correlated with Age, Selenium and Cholesterol, in Inuit of Greenland. A Pilot Study.", *BioFactors 9*, pp. 319–323 (1999).
Niibori, et al., "Bioenergetic Effect of Liposomal Coenzyme $Q_{10}$ on Myocardial Ischemia Reperfusion Injury", *BioFactors 9*, pp. 307–313 (1999).
Tomasetti, et al., "Distribution of Antioxidants Among Blood Components and Lipoproteins: Significance of Lipids/$CoQ_{10}$ Ratio as a Possible Marker of Increased Risk for Atherosclerosis". *BioFactors 9*, pp. 231–240 (1999).
Chida, et al., "In vitro Testing of Antioxidants and Biochemical End–Points in Bovine Retinal Tissue", *Ophthalmic Research*, 31: 407–415 (1999).
Bianchi, et al., "Oxidative Stress and Anti–Oxidant Metabolites in Patients with Hyperthyroidism: Effect of Treatment", *Horm. Metab. Res.*, 31: 620–624 (1999).
Al–Bekairi, et al., "Coenzyme $Q_{10}$ Ameliorates the Hepatic Toxicity Induced by Carbon Tetrachloride in Mice", *Research Communications in Pharmacology and Toxicology*, vol. 4, Nos. 3 & 4, pp. 163–171 (1999).
Yokoyama, et al., "Coenzyme $Q_{10}$ Protects Coronary Endothelial Function from Ischemia Reperfusion Injury Via an Antioxidant Effect", *Surgery*, vol. 120, No. 2, pp. 189–196 (1996).
Morita, et al., "Studies of Hypoxemic/Reoxygenation Injury: Without Aortic Clamping VII. Counteraction of Oxidant Damage by Exogenous Antioxidants: Coenzyme $Q_{10}$", *The Journal of Thoracic and Cardiovascular Surgery*, , vol. 110, No. 4, Part 2, pp. 1221–1227 (1995).
Lass, et al., "Effects of Coenzyme $Q_{10}$ and α–Tocopherol Administration on Their Tissue Levels in the Mouse: Elevation of Mitochondrial α–Tocopherol by Coenzyme $Q_{10}$", *Free Radical Biology & Medicine*, vol. 26, Nos. 11/12, pp. 1375–1382 (1999).

(List continued on next page.)

*Primary Examiner*—Leon B. Lankford, Jr.
*Assistant Examiner*—Ruth A. Davis
(74) *Attorney, Agent, or Firm*—Hoffmann & Baron, LLP

(57) ABSTRACT

A composition is provided that includes an ubiquinone, such as $CoQ_{10}$, bound by a glycoprotein matrix. A method is also provided for the manufacture of a composition of the invention. The glycoprotein matrix can be formed by permitting the growth of glycoprotein producing bacteria in the presence of the ubiquinone. The composition of the invention provides a method for increasing the stability and bioactivity of the ubiquinone. A method is also provided for administering an ubiquinone to a host by utilizing a composition of the invention.

9 Claims, No Drawings

OTHER PUBLICATIONS

Nielsen, et al., "No Effect of Antioxidant Supplementation in Triathletes on Maximal Oxygen Uptake, $^{31}$P–NMRS Detected Muscle Energy Metabolism and Muscle Fatigue", *Int. J. Sports Med.*, 20:154–158 (1999).

Alleva, et al., "Oxidation of LDL and Their Subfractions: Kinetic Aspects and $CoQ_{10}$ Content", *Molec. Aspects Med.*, vol. 18 (Supplement), pp. S105–s112 (1997).

Tomasetti, et al., "Coenzyme $Q_{10}$ Enrichment Decreases Oxidative DNA Damage in Human Lymphocytes", *Free Radical Biology & Medicine*, vol. 27, Nos. 9/10, pp. 1027–1032 (1999).

Aejmelaeus, et al., "Ubiquinol–10 and Total Peroxyl Radical Trapping Capacity of LDL Lipoproteins During Aging: the Effects of Q–10 Supplementation", *Molec. Aspects Med.*, vol. 18 (Supplement), pp. s113–s120 (1997).

Kagan, et al., "Coenzyme Q10 Can in Some Circumstances Block Apoptosis, and This effect is Mediated through Mitochondria", *Annals New York Academy of Sciences*, pp. 31–47.

* cited by examiner

UBIQUINONE COMPOSITION AND METHODS RELATED THERETO

BACKGROUND OF THE INVENTION

The present invention relates to ubiquinone compositions that can be used to deliver ubiquinones to a host and to methods of making such compositions.

Ubiquinones, such as Coenzyme $Q_{10}$ (hereinafter "$CoQ_{10}$"), are essentially a vitamin-like substance. $CoQ_{10}$ is found in small amounts in a wide variety of foods and is synthesized in all tissues. The biosynthesis of $CoQ_{10}$ from the amino acid tyrosine is a multi-stage process requiring eight vitamins and several trace elements. Co-enzymes are co-factors upon which comparatively large and complex enzymes depend for their function. $CoQ_{10}$ is the co-enzyme for at least three mitochondrial enzymes (complexes I, II and III) as well as enzymes in other parts of the cell.

Mitochondrial enzymes of the oxidative phosphorylation pathway are essential for the production of adenosine triphosphate (ATP), upon which all cellular functions depend. $CoQ_{10}$ plays a critical role in the sequential transfer of electrons in the mitochondrion.

In addition to electron transport in the mitochondrion, $CoQ_{10}$ has also been found to be important in the prevention of cellular-free radical damage, oxygenation at the cellular level, as well as other benefits.

Studies have demonstrated that sufficient levels of $CoQ_{10}$ promote optimal cell function in the human body. Significantly decreased levels of $CoQ_{10}$ have been noted in a wide variety of diseases in both animal and human studies. $CoQ_{10}$ deficiency may be caused by insufficient dietary $CoQ_{10}$, impairment in $CoQ_{10}$ biosynthesis, excessive utilization of $CoQ_{10}$ by the body, or any combination.

Various $CoQ_{10}$ formulations and methods of administration have been evaluated in clinical settings and demonstrate the potential and versatility of $CoQ_{10}$ compositions for a broad spectrum of disorders. $CoQ_{10}$ has been labeled a "breakthrough" drug in congestive heart failure—showing clinical benefit in 75% of Drugs Exp. Clin. Res., 11: 557–76 (1985)). $CoQ_{10}$ has been used to combat the effects of muscular dystrophy, producing clinical benefit in a subpopulation of patients with Duchenne form (Folkers, et al., Proc. Natl. Acad. Sci. U.S.A., 82: 4513–6 (1985)). $CoQ_{10}$ has been successfully utilized to battle periodontal disease (Wilkinson, et al., Res. Commun. Chem. Pathol. Pharmacol., 14: 715–9 (1976)). $CoQ_{10}$ has been implicated in the reduction in toxicity of chemotherapeutic drugs, e.g., cardiac toxicity of adriamycin (R. Ogura, et al., J. Nutr. Sci. Vitaminol., 28: 329–34 (1982)). $CoQ_{10}$ has been successfully implemented in the correction of drug-induced deficiencies, e.g., psychotherapeutic, diabetes and beta-blocker drugs (Katsumoto and Inoue, Jpn. Circ. J., 47: 356–62 (1983)). $CoQ_{10}$ has been used in immune restoration, e.g., aging, AIDS, allergies (Suzuki, et al., Jpn. J. Surg., 16: 152–5 (1986); Folkers, et al., Res. Commun. Chem. Pathol. Pharmacol., 38: 335–8 (1982); Folkers, et al., Biochem. Biophys. Res. Commun., 193: 88–92 (1993)).

$CoQ_{10}$ supplementation can be beneficial at any age, but due to statin-types of hyperlipidimia medications removing naturally occurring $CoQ_{10}$ from the body and the age related depletion of the body's natural resources of $CoQ_{10}$ by age 35, $CoQ_{10}$ supplementation may be most beneficial to those above age 35. Studies have shown that a decrease in $CoQ_{10}$ levels by 25% results in an inability of the body to produce enough cellular energy to remain healthy. A decline of 75% in $CoQ_{10}$ can be fatal.

Ubiquinones, including $CoQ_{10}$, are essentially insoluble in aqueous media. This insolubility may be attributed to the long hydrocarbon isoprenoid side chain which provides the molecule with its extremely lipophilic characteristics. These characteristics, among other effects, appear to be the source of the very slow absorption rates of the molecule. Pharmacokinetic data has demonstrated that intestinal absorption of ubiquinones is slow and ineffective in human subjects. By way of example, after administration of $CoQ_{10}$ there is a lag time of about 1 hour before increased plasma levels of $CoQ_{10}$ can be detected. A second absorption peak appears after about 24 hours. Approximately seven days of administration is required to achieve maximum steady-state plasma levels. Furthermore, absorption of orally administered $CoQ_{10}$ is variable and generally in the range of only about 2–5%.

Others have primarily focused on the production of the fatty emulsion of $CoQ_{10}$ in order to increase bioavailability and stability of $CoQ_{10}$. All of these formulations contain emulsifying agents. In fact, none of these $CoQ_{10}$ formulations are free of detergents or surfactants. Further, because of the nature of the oil emulsion, these formulations provide limited bioavailability in concentrations of $CoQ_{10}$ to the desired delivery sites in the body. Generally, oil formulations are highly viscous formulations with relatively low $CoQ_{10}$ concentration and accumulates slowly into cell membranes; commonly no more than 10 mg per ml. More importantly, emulsions are slowly absorbed and accumulate at low levels in cells.

Therefore, there remains a need for ubiquinone-containing compositions, for example compositions containing $CoQ_{10}$, with improved stability and bioactivity characteristics.

SUMMARY OF THE INVENTION

In accordance with the present invention, an ubiquinone composition is provided. The composition includes a glycoprotein matrix bound to the ubiquinone. In a preferred embodiment, the ubiquinone is $CoQ_{10}$. The glycoprotein matrix can be produced by microorganisms, such as yeast or bacteria. Preferred microorganisms are Saccharomyces cervisiae and bacteria within the genus Lactobacillus. The composition of the invention can also include stabilizers or additives to improve its properties. For example, in a preferred embodiment, the composition of the invention also includes a bioflavanoid, such as hesperidin, as a stabilizer.

A nutritional supplement is also provided. As discussed above, ubiquinones, such as $CoQ_{10}$, have been shown to be beneficial for health. The nutritional supplement includes the ubiquinone composition of the invention, having a glycoprotein matrix bound to the ubiquinone.

A method is also provided for preparing an ubiquinone-containing composition. The method includes binding at least one ubiquinone to a glycoprotein matrix. In a preferred embodiment, the glycoprotein matrix is formed by glycoprotein producing microorganisms. Thus, the binding includes contacting the ubiquinone with a glycoprotein producing microorganism under conditions such that the microorganism will produce glycoprotein.

The ubiquinone composition of the invention demonstrates improved properties as compared to commercially available ubiquinone compounds. Thus, a method is also provided for increasing the bioactivity of ubiquinone. A separate method is similarly provided for increasing the stability of ubiquinone. Both methods include binding the ubiquinone, such as $CoQ_{10}$, to a glycoprotein matrix.

A method is also provided for delivering an ubiquinone compound to a host. The method includes binding the ubiquinone with a glycoprotein matrix to form an ubiquinone-containing composition and administering the composition to the host.

DETAILED DESCRIPTION OF THE INVENTION

In accordance with the present invention, a composition is provided which includes an ubiquinone, such as $CoQ_{10}$, or a derivative thereof, and a glycoprotein matrix. The composition of the invention provides improved stability and bioactivity characteristics.

Ubiquinones are a group of lipid soluble benzoquinones some of which are involved in mitochondrial electron transport. Structurally, ubiquinones have a 2,3-dimethoxy-5-methylbenzoquinone nucleus and a variable terpenoid side chain containing from one to twelve mono-unsaturated trans-isoprenoid units (see the general structure below). The differences in properties among ubiquinones has been attributed to the difference in length of the terpenoid side chain. A dual nomenclature exists for these compounds and is based upon the length of the terpenoid side chain. A benzoquinone of this family is therefore properly referred to as either "Coenzyme $Q_n$," where n is an integer from one to twelve and designates the number of isoprenoid units in the side chain, or alternatively, "ubiquinone (x)" where x designates the total number of carbon atoms in the side chain and is a multiple of five. For example, the most common ubiquinone in animals has a ten isoprenoid side chain and is referred to as either Coenzyme $Q_{10}$ or ubiquinone (50).

The term "ubiquinone" includes compounds represented by the following general formula 1:

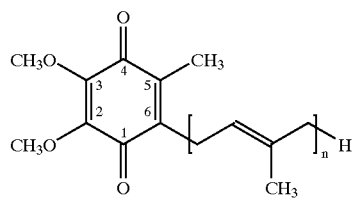

wherein typically n=1–12, preferably n=6–12, and most preferably n=10. Ubiquinones utilized in the present invention may be isolated in nature where n=6–10, or synthetically produced where n=1–12 using any one of several methods, including, by way of example, those described in Ramasara, *Coenzyme Q Biochemistry, Bioenergetics and Clinical Applications of Ubiquinone*, G. Lenz (ed.), John Willey & sons, New York, Ch. VI, pp. 131–144 (1985); Gibson and Young, *Methods in Enzymology*; and Fleischer and Packer (eds.), Academic Press, New York, pp. 600–609 (1978). One of ordinary skill in the art will appreciate that changes may be made to the ubiquinone to form a derivative without altering the antioxidant function thereof.

The term "ubiquinone" as used herein includes derivatives thereof. Referring to the general ubiquinone formula above, derivatives would include, for example, modifications of the methyl group at $C^5$, the methoxy groups at $C^2$ and $C^3$, as well as modifications of the isoprenoid side chain at $C^6$. Generally, these small changes would not significantly adversely alter the functional properties of the ubiquinone. More specifically, the modification at one or more of these positions will not adversely affect the oxidation-reduction properties of the modified ubiquinone so as to significantly diminish its anti-oxidant characteristics. In addition, such small changes in the isoprenoid side chain will not adversely affect the lipophilic characteristics of the modified ubiquinone. Accordingly, small changes resulting from modification of the substituents of a particular ubiquinone's benzoquinone nucleus are included within the scope of the ubiquinones in the present invention.

Examples of derivatives also include, for example, modification or substitution of the $C^5$ methyl group, the $C^2$ and $C^3$ methoxy groups, or the isoprenoid side chain with additional substituents, such as lower alkyl groups having from one to six carbons including branched, cyclic and straight chain alkyl groups; aryl substituents including phenyl and substituted phenyl substituents; aralkyl substituents including benzyl and tolyl substituents; halogen substituents including fluoro substituents; oxygen substituents including hydroxy, lower alkoxy, ether, and ester substituents; nitrogen substituents including amino and amido substituents; sulfur substituents including thiol, thioether, and thioester substituents. In addition to substituting the $C^5$ methyl group and/or the $C^2$ and $C^3$ methoxy groups with the above noted substituents, replacement of these groups with these substituents provides ubiquinones that are also included within the scope of this invention.

In a composition of the invention, a glycoprotein matrix is bound to at least one ubiquinone. $CoQ_{10}$ is the preferred ubiquinone. The glycoprotein matrix molecules are believed to be bound to the ubiquinone molecules by weak covalent bonds.

The composition can contain essentially any percentage of ubiquinone as desired. For example, the percentage of ubiquinone can vary between 1 and 99% by weight of the composition. In a preferred embodiment, the composition will contain between about 5 and 15% of ubiquinone by weight of the composition. Approximately 8% ubiquinone by weight of the composition is most preferred.

The glycoprotein matrix is the glycoprotein to which the ubiquinone compound is bound. Gycoprotein is a composite material made of a carbohydrate group and a simple protein. The carbohydrate in the glycoprotein can be any suitable carbohydrate, such as a monosaccharide, disaccharide, oligosaccharide, or polysaccharide. Oligosaccharide is preferred. The protein of the glycoprotein can any suitable polypeptide. The ratio of carbohydrate to protein in the glycoprotein matrix can vary, for example, from 99:1 to 1:99 by weight. A ratio of approximately 1:1 is preferred.

The ratio of glycoprotein matrix to ubiquinone can also vary. It is preferred that the ratio of glycoprotein matrix to ubiquinone will be such that nearly all of the ubiquinone in the composition is bound by glycoprotein matrix. In order to bind all or nearly all of the ubiquinone, applicants have found that a ratio of glycoprotein matrix to ubiquinone of approximately 6:1 by weight works well. However, to ensure that essentially all of the ubiquinone is bound, higher ratios of glycoprotein matrix to ubiquinone can be used, e.g. 10:1. The invention also contemplates a composition where there may be insufficient glycoprotein to bind all of the ubiquinone. In such cases, the ratio of glycoprotein matrix to ubiquinone can be less, e.g. 1:1.

In a preferred embodiment, the source of the glycoprotein matrix is a microorganism and, therefore, a preferred composition of the invention will include microorganisms. At the end of the manufacturing process of the composition, these microorganisms are usually inactive.

As discussed more specifically below, the glycoprotein matrix can be bound to the ubiquinone by allowing the microorganism to ferment, in the presence of the ubiquinone. As used herein, fermentation is the process by which microorganisms metabolize raw materials, such as amino acids and carbohydrate, to produce glycoprotein.

The microorganisms produce glycoprotein both intracellularly and extracellularly The intracellular glycoprotein will mainly be located in the cytoplasm of the microorganism or become part of the microorganism's physical structure. The glycoprotein from the microorganism that forms the glycoprotein matrix is mainly extracellular and, therefore, is available to be bound to ubiquinone.

Microorganisms that produce a glycoprotein matrix include yeast and some bacteria. A preferred yeast is *Saccharomyces cervisiae*. Bacteria that produce glycoprotein include bacteria within the genus Lactobacillus. For example, such bacteria include, but are not limited to, *Lactobacillus acidophillus, Lactobacillus bulgaricus, Lactobacillus caucasicus*, and *Bacterium bifidus*. Preferred bacteria include *Lactobacillus acidophillus*, and *Bacterium bifidus*.

In a separate preferred embodiment, the composition includes a bioflavanoid. Bioflavanoids have similar characteristics to ubiquinone and, therefore, act to stabilize the composition. A bioflavanoid is a group of naturally occurring substances thought to maintain normal conditions in the walls of small blood vessels. Bioflavanoids are widely distributed among plants, especially citrus fruits (hesperidin), black currants (rutin) and rose hips (quercitin). The bioflavanoid can also act to increase the production of glycoprotein by the microorganism. A preferred bioflavanoid is hesperidin.

The amount of bioflavanoid should be sufficient to achieve the desired stabilizing results. For example, the preferred range of amount of bioflavanoid in the composition of the invention can vary from approximately 5–15% by weight of the composition. An amount of approximately 6% by weight of the composition is most preferred.

The invention also includes a nutritional supplement that includes a composition of the invention as described above. It is known to administer ubiquinone and, specifically, $CoQ_{10}$, for the treatment or prevention of various ailments. Thus, the nutritional supplement should contain an amount of the composition such that a sufficient amount of ubiquinone is administered to achieve the desired result. Such amounts can be determined by one skilled in the art.

The composition of the invention can be manufactured so as to be biocompatible. Since the nutritional supplement is to be ingested, the microorganism used to produce the glycoprotein should be suitable for consumption by mammals, especially humans. Examples of such microorganisms include *Lactobacillus acidophillus* and *Saccharomyces cervisiae*. The nutritional supplement can also include pharmaceutically acceptable buffers, excipients, diluents, adjuvants, flavorings, and the like.

A method of preparing an ubiquinone-containing composition is also provided. The method includes binding a glycoprotein matrix to at least one ubiquinone.

In a preferred embodiment, the binding of the glycoprotein matrix to the ubiquinone includes contacting the ubiquinone with a glycoprotein producing microorganism under conditions in which the microorganism produces glycoprotein. The microorganisms require a medium in which to ferment and produce glycoprotein. Such media are known to those skilled in the art, and are usually liquid. Water is preferred. The microorganism solution should contain enough growth medium so as to allow for efficient growth of the microorganisms, as is known in the art. For example, to produce approximately 4 kg of a composition of the invention, approximately 4 liters of $H_2O$ can be used in the microorganism solution. When the microorganisms are added to the liquid medium, a microorganism solution is formed.

A microorganism solution is prepared in which the microorganisms will produce glycoprotein. The microorganisms are added to an appropriate medium that will allow microorganism growth, such as $H_2O$. The number of colony forming units of microorganism added to the medium will vary based upon the type of microorganism used. Any suitable microorganism can be used that produces a glycoprotein matrix. It is preferred that the microorganism used be acceptable for administration to humans and mammals and, more preferably, be acceptable for consumption. For example, *Saccharomyces cervisiae*, also known as baker's yeast, can be used as the first microorganism.

Combinations of microorganisms can be used provided that at least one of the microorganisms produces glycoprotein. When using combinations of microorganisms, the growth of one type of microorganism should not prevent the growth of the other. For example, various types of different yeast that produce glycoprotein can be used. Also, yeast and bacteria can be combined to produce glycoprotein. This combination is particularly advantageous because various types of bacteria, such as *Lactobacillus acidophillus*, also produce glycoprotein.

A sufficient amount of colony forming units should be added to the microorganism solution to bind at least some of the ubiquinone. If the composition of the invention is to contain a small amount of ubiquinone, fewer microorganisms will be required to bind the ubiquinone with glycoprotein matrix. It is preferred that enough colony forming units be added to the microorganism solution to bind essentially all of the ubiquinone with glycoprotein matrix. One skilled in the art can determine such amounts. For example, when using baker's yeast to create a glycoprotein matrix to bind essentially all of the ubiquinone, approximately 375 g baker's yeast having approximately 10 billion colony forming units per gram can be added to 4 liters of aqueous medium containing 475 g $CoQ_{10}$ to be bound.

The microorganisms that produce the glycoprotein require nutrients to efficiently grow, multiply, and form glycoprotein by metabolizing the nutrients. The nutrients can be directly added to the microorganism solution or can be added to a nutrient media, which is then added to the microorganism solution.

Amino acids are one nutrient necessary for efficient glycoprotein production. The amino acids are metabolized by the microorganisms and ultimately become part of the polypeptide within the glycoprotein matrix. The amino acids should include those that are suitable for the manufacture of glycoprotein. Such amino acids include, but are not limited to, glutamine, lysine, cysteine and methionine, aspartic acid, leucine, valine, alanine, arginine, and glycine. The amino acids need not be in a pure form, but can be added as part of a stable compound. Examples of amino acid compounds that can be used are L-Glutamic Acid, L-Lysine HCl, L-Cysteine HCl and DL-Methionine.

The amount of amino acids will vary based upon the amount and percentage of ubiquinone desired to be bound by glycoprotein matrix. For example, if essentially all of the ubiquinone is to be bound by glycoprotein matrix, the ratio of amino acids to ubiquinone in the microorganism solution will usually be approximately 2:1 by weight.

Carbohydrate is another nutrient necessary for the efficient production of glycoprotein by the microorganism. As with the amino acids, the carbohydrate can be added to a nutrient media, which is then added to the microorganism solution, or can be added directly to the microorganism solution. Carbohydrates beneficial for the production of glycoprotein are known in the art. The carbohydrate can be, for example, a polysaccharide, oligosaccharide, disaccharide or monosaccharide or combinations thereof. Examples of appropriate carbohydrates include, but are not limited to, maltose and gum acacia. Maltose is most preferred.

The amount of carbohydrate added to the nutrient media or microorganism solution will vary depending upon the complexity and molecular weight of the carbohydrate added to the solution. The amount of carbohydrate should be sufficient to permit the microorganisms to produce the glycoprotein matrix. The amount of carbohydrate necessary will also vary based upon the amount and percentage of ubiquinone desired to be bound by glycoprotein matrix. For example, when it is desired to bind essentially all of 475 g of ubiquinone, it is preferred that carbohydrate be added in an amount between about 100 to 150 grams per liter of aqueous medium solution.

The binding of the ubiquinone occurs in the microorganism solution as the glycoprotein is being produced by the microorganisms. Thus, the microorganism solution will contain the ubiquinone to be bound by glycoprotein matrix. The ubiquinone is added before or soon after fermentation of the microorganisms begins.

If desired, appropriate additives may be included to the microorganism solution. The amount of additive would be the amount necessary to obtain the desired beneficial result, without diminishing the viability of the microorganism or the production of glycoprotein by the microorganim. The amounts of such additives can be determined by one skilled in the art.

Such additives may include, for example, stabilizers. Stabilizers are substances that improve the stability of the $CoQ_{10}$. One example of such a stabilizer is bioflavanoids. Preferred bioflavanoids include hesperidin, quercitin and rutin. Since these bioflavanoids are naturally obtained, commercially available bioflavanoids very often will include additional materials such as fibers or cellulose. The active portion, e.g. hesperidin, quercitin, or rutin, will make up a percentage of the bioflavanoid. The active ingredient in the bioflavanoid will usually vary between approximately 10–60%. When using a natural bioflavanoid as a stabilizer, an amount of between about 500 to about 1000 g per 425 g of ubiquinone is preferred. Approximately 825 g of bioflavanoid per 425 g of ubiquinone is most preferred.

Other additives can be added which, for example, improve the viability of the microorganisms that produce the glycoprotein or increase the yield of glycoprotein that becomes bound to the ubiquinone. For example, salts can be added in order to increase the viability of the microorganism. Such salts include, but are not limited to, calcium carbonate, ammonium sulfate, and magnesium sulfate. Calcium carbonate is preferred. The amount of salt added to the microorganism solution should be sufficient to obtain the desired result of improving the viability of the organism, as is known in the art. A preferred range of salt added to the microorganism solution is between about 25 to about 150 grams of salt per 375 grams of microorganism, such as *Saccharomyces cerivisiae*. Approximately 40 g of salt per 375 gram of microorganism is most preferred.

In a preferred embodiment, substances are added to the microorganism mixture that will further induce the growth of the microorganisms and the fermentation resulting in the formation of a glycoprotein matrix. For example, it may be beneficial to add a nutritional substance to the microorganism mixture. Examples of such nutritional substances include soy flour and nutritional yeast, such as inactive baker's yeast or inactive brewer's yeast. When using soy four, non-genetically modified organism (non-GMO) soy flour is preferred. Such nutritional substances feed the microorganisms, thereby inducing growth and the manufacture of glycoprotein.

The method of the invention does not require that the ingredients ultimately forming the microorganism solution be added in any particular order. For example, as discussed above, the amino acids and carbohydrate metabolized by the microorganisms can each be added to a nutrient media that is added to the microorganism solution or can be added directly to the microorganism solution. Also, the ubiquinone can be directly added to the microorganism solution or can be added to a nutrient media that is then added to the microorganism solution.

If a nutrient media is prepared, it is preferred that the nutrient media include at least the amino acids. The nutrient media can also include other ingredients, for example, the ubiquinone, carbohydrate, salt, and stabilizer. Also, in order to create a more homogenous nutrient media, the temperature of the nutrient media can be raised. However, the temperature of the nutrient media should remain below the temperature at which the components of the nutrient media will decompose. For example, a nutrient media containing amino acids, $CoQ_{10}$ and bioflavanoid can be heated to a temperature of about 130° F. before being added to the microorganism solution. If the nutrient media is heated, it should be allowed to cool, e.g. to about 95° F., before being added to the microorganism solution. Also, the nutrient media should be added slowly to the microorganism solution so as to minimize the disturbance of the microorganisms in solution.

The microorganism solution should be maintained under conditions that permit optimal microorganism growth. For example, a temperature range of between about 90–95° F. is suitable for most glycoprotein producing microorganisms. The microorganisms should also be permitted to ferment for a sufficient period of time to produce the desired amount of glycoprotein matrix. As discussed above, this time will vary based upon, among other factors, the amount and percentage of ubiquinone to be bound by glycoprotein matrix. For example, in order to fully bind 475 g ubiquinone, applicants allowed a microorganism solution containing 375 g active baker's yeast to ferment for approximately four hours at 90–95° F.

In a preferred embodiment, a proteolytic enzyme is added to the microorganism solution after the microorganisms in the microorganism solution have been permitted to ferment. Suitable proteolytic enzymes include, but are not limited to, papain, bromelain, pepsin or fungal protease. Without being bound by theory, it is believed that the proteolytic enzymes assist in breaking down the cell wall of the microorganisms. This breaking down of the cell wall of the microorganism may help in releasing the glycoprotein produced by the microorganism and improves the digestibility of the final composition in humans.

The amount of proteolytic enzyme added to the microorganism solution should be sufficient to break down the cell wall of the first microorganism, but should not affect the integrity of the glycoprotein produced by the microorganism. This amount will vary depending upon the number of microorganisms in the microorganism solution. Typically, approximately 1 to 50 g of proteolytic enzyme will be added per 500 g microorganism.

Additional microorganisms can be added to the microorganism solution after the first microorganisms are added. It is preferred that the additional microorganisms be added after the first microorganisms have been permitted to ferment, but before the microorganism solution has been dehydrated. In a preferred embodiment, the additional microorganisms also produce glycoprotein. Therefore, after the additional microorganisms are added to the microorganism solution, the solution should be maintained at a temperature and conditions so as to permit the growth and fermentation of both the first and additional microorganisms. Such conditions are known in the art and will usually coincide with the growth conditions for the first microorganisms, as discussed above.

Bacteria can be utilized as an additional microorganism. As with the first microorganisms, it its preferred that the additional microorganisms be suitable for administration to mammals and, more preferably, suitable for human consumption. Examples of such bacteria are bacteria of the genus Lactobacillus, for example *Lactobacillus acidophillus*.

The appropriate number of colony forming units of the additional microorganisms can be determined by one skilled in the art. For example, when *Lactobacillus acidophillus* and *Bacterium bifidus* are introduced as additional microorganisms, approximately 125 g of bacteria per 475 g of ubiquinone can be added having approximately 4 billion colony forming units per gram of bacteria.

Due to the medium used to grow the microorganisms, the microorganism solution will usually be in the form of an aqueous mixture or solution. When the microorganism solution is in the form of an aqueous solution, it is preferred that the microorganism solution be dehydrated after fermentation has taken place and the ubiquinone has been bound by the glycoprotein matrix. Methods of dehydrating solutions are known in the art. For example, such methods include freeze-drying, spray drying, open air drying, and drum drying. Spray drying is preferred. A longer dry time may be necessary depending on various factors, such as total water content, equipment used, and atmospheric humidity. However, after dehydrating the microorganism solution, the resulting product should be a fine powder, which can then be manufactured into a pill or other form suitable for administration.

The microorganism solution can be homogenized to produce a more uniform product. The homogenization is performed after the production of glycoprotein matrix, usually before dehydrating the microorganism solution. Methods of such homogenization are known in the art. For example, homogenization can be performed by a homogenization pump, shearing pump or, if produced in a small batch, a blender.

In a preferred embodiment, the microorganisms are deactivated before dehydrating, preferably by raising the temperature of the microorganism solution. For example, the preferred temperature and conditions for stopping the fermentation in a mixture containing *Saccharomyces cervisiae* and Lactobacillus bacteria is heating the mixture to approximately 160 to 170° F. for approximately three hours with stirring.

It has been discovered that binding the ubiquinone to a glycoprotein matrix as in the composition described increases the bioactivity of the ubiquinone. Therefore, a separate embodiment of the invention includes a method for increasing the bioactivity of an ubiquinone by binding the ubiquinone with a glycoprotein matrix. The ubiquinone composition of the invention will allow the ubiquinone to have an increased effect on the organism to which the composition is administered.

For example, it is known that $CoQ_{10}$ can have an antioxidative effect. As described in Example 2, compositions of the invention having $CoQ_{10}$ bound to a glycoprotein matrix were found to have antioxidant activity approximately 20 times that of commercial $CoQ_{10}$.

It has also been discovered that binding the ubiquinone to a glycoprotein matrix as in the composition of the invention can increase the stability of the ubiquinone. Therefore, a separate embodiment of the invention includes a method for increasing the stability of an ubiquinone by binding the ubiquinone with a composition of the invention.

As with other vitamin or vitamin-like substances, ubiquinone can deteriorate when exposed to air. By binding the ubiquinone with a glycoprotein matrix, this deterioration is decreased. As demonstrated in Example 3, the composition of the invention lost only half as much $CoQ_{10}$ over 36 days compared to commercial $CoQ_{10}$ when exposed to open air at 50° C.

In a separate embodiment, a method of delivering an ubiquinone compound to a host is provided. The method includes binding a glycoprotein matrix to the ubiquinone to form a glycoprotein matrix bound ubiquinone composition. The composition is then administered to the host.

The ubiquinone composition can be administered topically or systemically. Systemic administration can be enteral or parenteral. Enteral administration is preferred. For example, the ubiquinone composition can be easily be administered orally. Liquid or solid (e.g., tablets, gelatin capsules) formulations can be employed. The formulation can include pharmaceutically acceptable excipients, adjuvants, diluents, or carriers. The composition can also be administered intravenously, with a suitable pharmaceutical carrier (vehicle) or excipient, as understood by those skilled in the art. Topical administration can be, for example, in a cream or emollient.

In a preferred embodiment the host is a mammal. Mammals include, for example, humans, as well as pet animals such as dogs and cats, laboratory animals such as rats and mice, and farm animals such as horses and cows. Humans are most preferred. Optimal doses of the ubiquinone can be determined by one skilled in the art based on a number of parameters including, for example, age, sex, weight, condition being treated, the severity of the condition, and the route of administration.

EXAMPLE 1

This example demonstrates the preparation of a composition of the invention. The particular method employs 5 kilograms of dry material to yield approximately 4 kg ubiquinone-containing composition.

A nutrient media containing $CoQ_{10}$ was first prepared. 110 g L-Glutamic Acid, 212 g L-Lysine HCl, 535 g DL-Methionine, and 45 g L-Cysteine HCl, and 40 g calcium carbonate were added slowly to 4 liters $H_2O$ heated to 140° F. After 30 minutes, 475 g $CoQ_{10}$, was added to the amino acid solution. The solution was stirred at about 130° F. for approximately 4 hours and allowed to cool to 95+/−2° F. 825 g of a natural bioflavanoid having 300 g hesperidine was then added.

An active yeast solution was then prepared. 375 g active baker's yeast, *Saccharomyces cervisiae* (~10 billion colony forming units per gram) was added to 4 liters $H_2O$ to form an aqueous solution. 125 g maltose and 625 g gum acacia were then added.

The nutrient media containing $CoQ_{10}$ was then inoculated very slowly into the active yeast solution to form a live fermented solution. The mixture was allowed to ferment for four hours at 90–95° F. 500 g nutritional yeast (inactive Baker's Yeast) and 1003 g soy flour (non-GMO) were added and the mixture was allowed to ferment for four hours at 90–95° F. 5 g proteolytic enzyme (Papain) was then added and allowed to react for 30 minutes. 125 g *Lactobacillus acidophillus* and *Bacterium bifidus* (~4 billion colony forming units/gram) were added to the live fermented solution and allowed to ferment for 1½ hours at 95+/−2° F. with constant stirring. Active fermentation was then stopped by heating the solution to 160–170° F. for three hours with stirring.

The solution was then homogenized in a shearing pump (Charles Ross & Sons Corp.) for approximately 1–2 hours and spray dried (NIRO, Nicholas Engineers Research Corp.) for approximately 4 hours. The resulting product was a fine brown to tan powder, which was analyzed for stability and bioactivity.

EXAMPLE 2

The bioactivity of a composition of the invention produced in Example 1 was examined relative to commercially available $CoQ_{10}$ (USP).

A weighed portion (50–500 mg) of solid sample of the composition of the invention was mixed with 5 ml of 50% methanol/water and heated at 90° C. in a plastic screw-capped tube with intermittent shaking for 2 hours to determine the unconjugated ("free") phenols present. Another weighed portion of the same sample was heated with 5 ml of 1.2 M HCl in 50% aqueous methanol for 2 hours at 90° C. to measure the unconjugated plus conjugated ("total") phenols. The extracts, each done in duplicate, were then filtered with a 0.45 µm filter and stored at −20° C. until assay. Values for free polyphenols and total phenols for commercial $CoQ_{10}$ are known.

The phenol content in the extracts was measured by the Folin-Cocialteu reagent (Sigma Chemical Co., St. Louis, Mo.) using catechin (Sigma) as a standard. A blank, catechin standards and samples were added to the Folin reagent in a cuvette and after 20 minutes the color was measured at 720 nm vs. a blank.

Quality of antioxidant activity was determined in a dose-response assay of the $IC_{50}$ value, i.e. the concentration of phenols in the extract to inhibit 50% of the oxidation of lower density lipoproteins (LDL+VLDL). This model is an in vitro model of atherosclerosis where the initial step is the oxidation of the lower density lipoproteins, i.e. the "bad" cholesterol. LDL+VLDL is isolated from the plasma of normocholesterolemic humans using an heparin-agarose affinity column (H-6508, Sigma). Extracts of antioxidants were added in duplicate at various concentrations (typically 0.05 to 15 µM) to LDL+VLDL (70 µg/ml of protein as measured vs. albumin standard with Coomasie Blue, Sigma). 25 µM of the oxidant cupric ion was then added, the solution made to a total volume of 400 µL with phosphate buffered saline, pH 7.4 (Sigma) and the solution left at 37° C. for 6 hours.

The amount of lipid peroxides was measured using thiobarbituric acid and fluorometry. The % of inhibition of lipid peroxide formation was calculated vs. a control with no added antioxidants. The $IC_{50}$ value in µM units was then calculated.

The amount of $CoQ_{10}$ in the composition of the invention was determined by HPLC using UV detector, C18 column (Perkin Elmer Pecosil 5, 15 cm) and a solvent of 75% methanol and 25% isopropanol.

The results are set forth in Table 1 below. The higher the $1/IC_{50}$ value, the better the quality of antioxidants.

The methods used are further described in: Vinson, J. A., and Hontz, B. A. Phenol antioxidant index: comparative antioxidant effectiveness of red and white wines, *J. Agric. Food Chem.*, 1995, 43, 401–403; Vinson, J. A., Jang, J., Dabbagh, Y. A., Serry, M. M., and Cai, S. Plant polyphenols exhibit lipoprotein-bound antioxidant activity using an in vitro model for heart disease. *J. Agric. Food Chem.*, 1995, 43, 2798–2799; and Steinberg, D., Parthasarathy, S., Carew, T. E., Khoo, J. C., and Witzum, J. L. Beyond cholesterol: modification of low density lipoprotein that increases its atherogenicity. *New Eng. J. Med.*, 1989, 320, 915–924; all of which are incorporated herein by reference.

TABLE 1

| SAMPLE | IC50 (uM) | 1/IC50 |
|---|---|---|
| $CoQ_{10}$ bound by glycoprotein contains 8.4% $CoQ_{10}$ | 0.064 (based on $CoQ_{10}$ conc.) | 15.6 |
| $CoQ_{10}$ (USP) | 1.33 | 0.751 |

The results demonstrate that the $CoQ_{10}$ composition of the invention bound to glycoprotein has an antioxidant activity that is 20 times better than commercially available $CoQ_{10}$.

EXAMPLE 3

The stability of the composition obtained in Example 1 was examined.

100 mg of USP $CoQ_{10}$ (Sigma) and a composition from Example 1 was placed in a 10 ml beaker in a 50° C. oven open to the air. The amount of $CoQ_{10}$ remaining was analyzed by HPLC using a C18 column (Perkin Elmer Pecosil 5, 15 cm) and a solvent of 75% methanol and 25% isopropanol. The results are set forth below in Table 2.

TABLE 2

| Sample | Loss of $CoQ_{10}$ at 0 days | Loss of $CoQ_{10}$ after 36 days at 50° C. (equivalent to 3 months at room temperature) | Loss of $CoQ_{10}$ after 72 days at 50° C. (equivalent to 6 months at room temperature) |
|---|---|---|---|
| USP $CoQ_{10}$ | 0% | 6.8% | 16.8% |
| $CoQ_{10}$ bound by glycoprotein | 0% | 3% | 14.7% |

After 36 days, the composition of the invention lost only half as much as the commercial $CoQ_{10}$ material, i.e. 3% vs. 6.8%. After 72 days, the composition of the invention lost 14.7% of its $CoQ_{10}$ vs. 16.8% $CoQ_{10}$ lost with the commercial sample. Therefore, the results show that the composition of the invention serves to increase the stability of the $CoQ_{10}$ contained therein.

While there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

I claim:

1. A composition comprising a glycoprotein matrix bound coenzyme Q10, wherein the glycoprotein matrix bound coenzyme Q10 is produced by fermenting yeast and bacteria suitable for consumption by mammals in the presence of coenzyme Q10, and subsequently isolating the glycoprotein matrix bound coenzyme Q10 from the fermentation medium.

2. A composition as described in claim 1, wherein said coenzyme Q10 is present in an amount between about 5% and 15% by weight of said composition.

3. A composition as described in claim 1, wherein the ratio of said glycoprotein matrix to said coenzyme Q10 is between about 1:1 to about 10:1.

4. A nutritional supplement comprising coenzyme Q10 bound by a glycoprotein matrix according to claim 1.

5. A composition comprising a glycoprotein matrix bound coenzyme Q10 and a bioflavonoid, wherein the glycoprotein matrix bound coenzyme Q10 is produced by fermenting yeast and bacteria suitable for consumption by mammals in the presence of coenzyme Q10, and subsequently isolating the glycoprotein matrix bound coenzyme Q10 from the fermentation medium.

6. A composition as described in claim 5, wherein said bioflavonoid is hesperidin.

7. A composition as described in claim 5, wherein said yeast include *Saccharomyces cerevisiae*.

8. A composition as described in claim 5, wherein said bacteria comprises bacteria within genus Lactobacillus.

9. A composition as described in claim 5, wherein said bacteria includes *Lactobacillus acidophilus* or *Bacterium bifidus,* or both.

* * * * *